United States Patent [19]
Ballintyn et al.

[11] Patent Number: 5,584,836
[45] Date of Patent: Dec. 17, 1996

[54] CANNULATED MEDICAL SUTURE ANCHOR

[75] Inventors: Nicolaas J. Ballintyn, Germantown; Tom Barker, Memphis; Abraham Salehi, Bartlett, all of Tenn.; Hansen A. Yuan, Fayetteville, N.Y.; Bryan Hildebrand, Cleveland Heights, Ohio

[73] Assignee: Smith & Nephew Richards, Inc., Memphis, Tenn.

[21] Appl. No.: 610,843

[22] Filed: Mar. 5, 1996

Related U.S. Application Data

[63] Continuation of Ser. No. 224,332, Apr. 7, 1994, abandoned.

[51] Int. Cl.$^6$ ..................................... A61B 17/56
[52] U.S. Cl. ................ 606/73; 606/77; 606/232
[58] Field of Search .................. 606/73, 72, 75, 606/77, 76, 53, 60, 61, 65, 67, 104, 232; 411/395, 402, 403, 410, 919, 411

[56] References Cited

U.S. PATENT DOCUMENTS

| | | | |
|---|---|---|---|
| 1,184,173 | 5/1916 | Gehring | 411/919 |
| 1,187,714 | 6/1916 | Corey | 411/919 |
| 1,300,275 | 4/1919 | Johnson | 411/919 |
| 2,168,000 | 8/1939 | Schaurte | 411/395 |
| 2,437,381 | 3/1948 | Cullen | 411/919 |
| 4,904,261 | 2/1990 | Dove et al. | 623/17 |
| 5,019,079 | 5/1991 | Ross | 606/73 |
| 5,156,616 | 10/1992 | Meadows et al. | 606/73 |
| 5,169,400 | 12/1992 | Mühling et al. | 606/73 |

FOREIGN PATENT DOCUMENTS

| | | | |
|---|---|---|---|
| 225815 | 9/1990 | Japan | 411/395 |
| 93/21848 | 11/1993 | WIPO | 606/73 |

*Primary Examiner*—Guy V. Tucker
*Attorney, Agent, or Firm*—Pravel, Hewitt, Kimball & Krieger

[57] ABSTRACT

Polymeric medical fixation screws with multiple cannulations and thereby a reduced risk of shearing while being torqued into place are provided. The polymeric screws have at least two cannulae, on either side of a central longitudinal axis of the screw, extending parallel to the longitudinal axis. Torquing instruments are inserted into the cannulae so that the applied torque force for driving the screws into a bone hole is distributed along the shaft of the screw. In one embodiment, the invention provides interference screws, while in other embodiments the invention provides medical fixation screws with heads and soft tissue-to-bone anchors or suture anchors. The polymeric screws may be fabricated from virtually any suitable biocompatible polymers or composites, including bioabsorbable polymers and their composites.

10 Claims, 2 Drawing Sheets

FIG.1A
FIG.1B
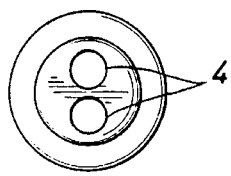
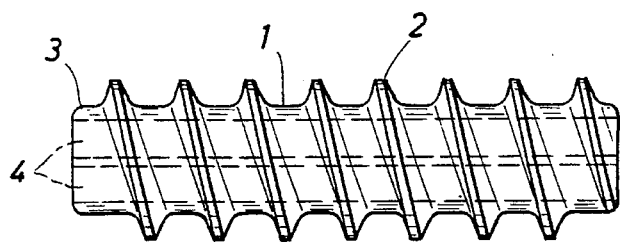
FIG.2A
FIG.2B
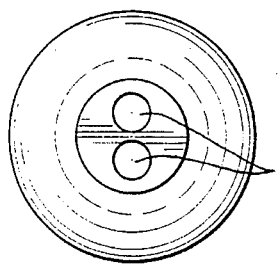
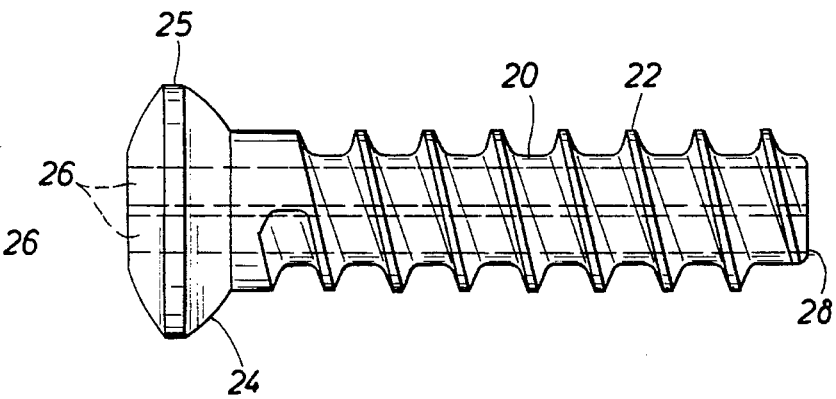
FIG.3A
FIG.3B
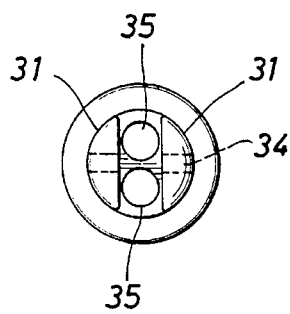
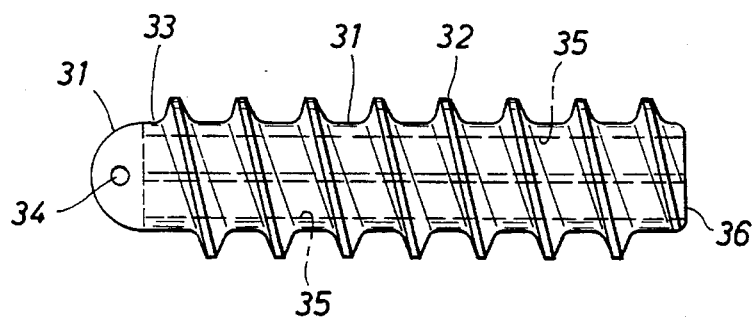

5,584,836

CANNULATED MEDICAL SUTURE ANCHOR

This is a continuation of application Ser. No. 08/224,332, filed Apr. 7, 1994 now abandoned.

BACKGROUND OF THE INVENTION

1. Field of the Invention

The invention relates to screws used in medical applications to affix medical implants, allografts, autografts or heterografts to bone structure of a patient. More specifically, the invention provides polymeric medical fixation screws with multiple cannulae for receiving means for applying torquing to the screws, such that the screws are subjected to reduced stresses while being torqued into place, thereby reducing the risk of shearing the screws.

2. Description of the Related Art

Medical screws of various designs and materials are used to affix medical implants, autografts, allografts or heterografts to bone structure of a patient. Depending upon the particular application, the medical screw may be headless (an interference screw) or be supplied with a suitable head (such as screws used to fix bone plates in place, anchor soft tissue to bone, and like applications). Medical screws are typically fabricated from biocompatible metal alloys or biocompatible organic polymers. Polymeric materials provide significant advantages over metal alloys in certain specific circumstances. In particular, when the polymer is bioabsorbable, then the requirement of a second surgical procedure to remove the screw, and any other temporarily needed implant device, is eliminated. Further, bioabsorbable implants and screws can be designed to facilitate improved bone healing by gradually transferring applied loads from a fixation device to the natural bone, as the device's material properties degrade at a predetermined rate. Therefore, the use of bioabsorbable medical screws is desirable in a wide range of applications.

Bioabsorbable screws being made of organic polymers, however, often have insufficient strength to withstand shear loads that must be applied during the insertion of the screw into a hole in bone. Efforts have been made to alleviate the shear stress problem by supplying the bone screws with heads having a recess for receiving an insertion tool with a non-circular cross-section, such as an hexagonal recess and matching tool. This screw may also be supplied with a bore for receiving a guide pin extending from the recess through the entire length of the screw to guide the screw into place. However, only the recess in the head of the screw is designed for torque transfer. Thus, stresses are concentrated in the vicinity of the head of the screw so that it is susceptible to shear failure in this region when it is being torqued into place.

Another approach, shown in U.S. Pat. No. 5,169,400, is a screw designed with a single, central non-circular cross-section cannula extending from the screw head, along the shank, to the tip. The non-circular cross-section of the cannula is essential to allow torque transfer. The cannula is disclosed as hexagonal, square, or star-shaped in cross-section. The cannula receives a torquing tool and the design is intended to distribute torque force over the entire length of the screw shaft when the screw is being torqued into place. Nevertheless, this design suffers from several disadvantages. These include peak tensile, compressive, and shear stresses located at adjacent sides of each corner within the cannula posing a significant risk of screw failure, especially since the corners coincide with the thinnest section of the screw body.

It is desirable to develop a polymeric medical screw that can be used to affix medical implants or grafts to the bone structure of a human patient. The screw should be able to withstand torquing force encountered in driving the screw into place in a hole in bone, with minimal risk of shear failure. Further, the screw should be convenient to use during surgical procedures.

SUMMARY OF THE INVENTION

The invention provides medical screws for affixing medical implants, allografts, autografts or heterografts to bone structure of a patient, with reduced risk of shear failure resulting from torquing the screws into place. The screws according to the invention are supplied with at least two cannulae, each offset from the center of the screw, extending along the longitudinal axis of the screw for at least a portion of the distance to the tip of the screw. These cannulae, which are preferably circular in cross-section, receive mating means for applying torque to turn the screw into place.

According to the invention, the screws may be supplied with heads for certain applications, such as affixing bone plates. Alternatively, the screws may be headless when used as interference screws, for example. In another embodiment, the screws have a means for engaging a suture so that the screw may be used as a soft tissue-to-bone anchor or suture anchor.

The screws of the invention provide the advantages of longitudinal distribution of torsional insertion loads, while eliminating the stress concentration effects encountered with screws that have a single, central non-circular cannula. Finite element analysis demonstrates that the screws of the invention have less than one-half the peak tensile stress of a screw with a single hexagonal cannula. They also have less than one-sixth the peak compressive stress, and less than one-third of the maximum shear stress. Further, whereas these stresses are located at adjacent sides of each corner of the single hexagon cannula comparative screw, posing a significant chance of failure, the peak stresses are located near the center of screws of the invention, thereby rendering them less susceptible to torsional failure. Thus, the invention provides medical fixation screws with multiple cannulae that are less susceptible to failure while being torqued into place during surgery.

BRIEF DESCRIPTION OF THE DRAWINGS

A better understanding of the present invention can be obtained when the following detailed description of the preferred embodiments is considered in conjunction with the following drawings, in which:

FIGS. 1A and 1B show end and side views of an embodiment of a dual cannulated interference screw according to the invention;

FIGS. 2A and 2B show end and side views of an embodiment of a dual cannulated headed fixation screw according to the invention;

FIGS. 3A and 3B show end and side views of an embodiment of a dual cannulated soft tissue-to-bone anchor or suture anchor according to the invention;

DETAILED DESCRIPTION OF THE PREFERRED EMBODIMENTS

Figure 4A:
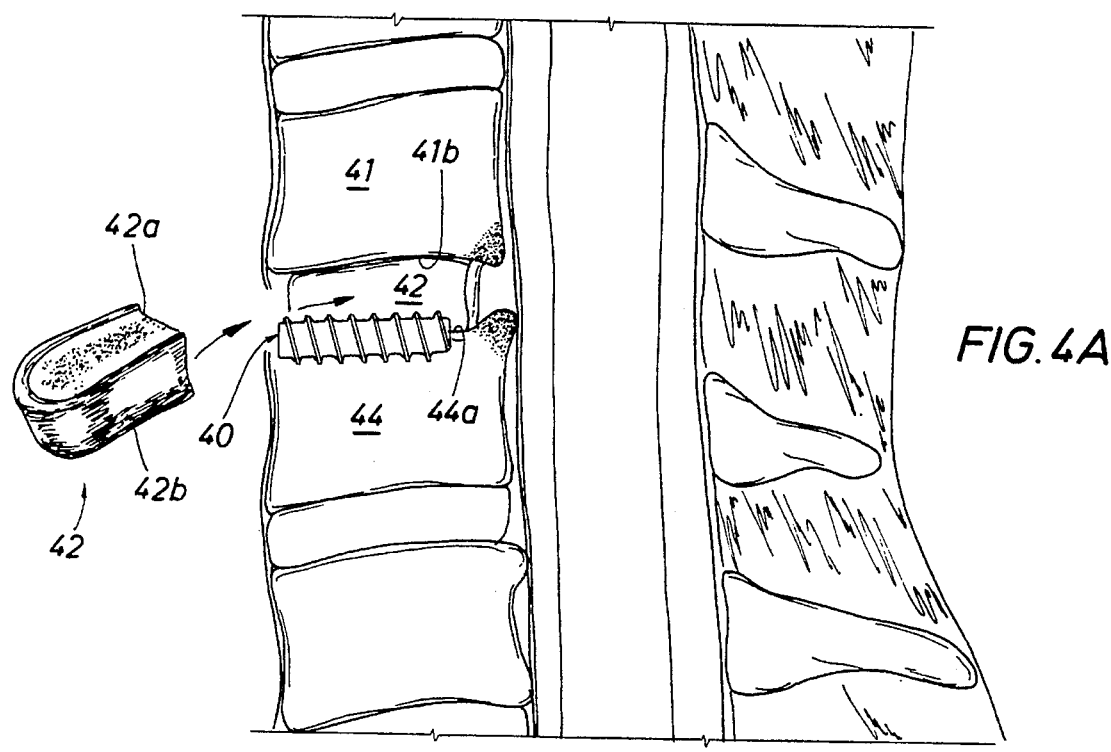
FIG. 4A is a schematic representation in partial cross-section of a screw according to the invention used as an interference screw in replacing a disc with a bone graft in back surgery.

The invention provides medical fixation screws having a reduced risk of shear failure while being torqued into place in a hole in bone. Preferably, these fixation screws are supplied with at least two cannulae extending from a head of a screw along at least a portion of a shank of the screw extending to a tip. The cannulae are sized to receive means for applying torque to the screws.

The screws may be made of any biocompatible polymer, such as polyaryletherketone, polysulfone, ultra high molecular weight polyethylene, polycarbonate, polyamide, polyolefin, polyethylene terephthalate, polybutylene terephthalate, copolymers of these terephthalates, polymethylmethacrylate, and the like. In certain specific instances, it may be desirable to use a bioabsorbable polymer, for example, poly α-hydroxy acids such as polyglycolic acid, polylactic acid, copolymers of lactic and glycolic acids, or polycaprolactone, polydioxanone polyalkylcarbonates, polyorthoesters, polyanhydrides, and the like.

Further, the screws of the invention may be fabricated from a composite that includes a matrix of a biocompatible polymer with a biocompatible reinforcement. The preferred non-bioabsorbable reinforcements include carbon fiber, graphite fiber, fibers of biocompatible polymers (e.g., those listed above), polyaramids, and the like. When a bioabsorbable polymer is used as a matrix, the preferred reinforcements are absorbable organic polymer fibers, absorbable glass, and absorbable ceramic fibers.

The screws according to the invention may be fabricated by any one of a number of methods. In certain instances, it may be desirable to fabricate the screws by injection molding a biocompatible polymeric composition around the means for applying torque to the screw. To use the screws in a surgical procedure, these means are engaged by a torquing tool for supplying torque to drive the screw into place. Thereafter, the means for applying torque may be removed from the screw, especially if the screw is of the bioabsorbable type. Alternatively, when the screw is not bioabsorbable, then the means for applying torque may be fabricated from a biocompatible metal alloy and may be left in place in the body. Preferably, in this instance, the portion of the means for applying torque that extends beyond the head or top end of the screw are clipped from the screw.

As an alternative, screws according to the invention may be molded or extruded and machined with at least two cannulae, using techniques known to those of ordinary skill in the art. Means for applying torque may then be inserted into the cannulae of the screw at the point when it is desired to torque the screw into place in the bone structure of a patient. Thereafter, the means for applying torque should be removed leaving the screw in place.

The means for applying torque is elongate and shaped to fit within the cannulae. Thus, examples of the means for applying torque are thin metal rods of circular, hexagonal, square, and the like cross-sections, to match and cooperate with the shape of the screw's cannula. Circular cross-section rods are preferred to cooperate with circular cross-section cannulae. The means for applying torque are of sufficient length to extend beyond the top end of the screw, when fully inserted, to allow a torquing tool to engage outward extending portions for torquing the screw into place.

The means for applying torque may be supplied with the screws or, alternatively, a torquing tool or driver may be fitted with an attachment that has means for applying torque and that is able to cooperate with cannulae in the screw to drive the screw into a bone hole. As a further alternative, the means for applying torque may be supplied with the screws and may be pre-attached to a fixture for cooperating with a chuck of a driving or torquing tool. After surgical insertion of the screw, the means for applying torque and attached fixture are detached from the screw.

Certain aspects of the invention may best be understood with reference to the accompanying drawings, which are illustrative of certain preferred embodiments. The headless cannulated interference screw of FIG. 1 has a body 1, a screw thread 2 extending along its outer surface, and a top-end 3. Two cannulae 4, equidistant from the center of the screw, extend along the entire length of the screw body 1. While the cannulae shown are circular, other cross-sectional shapes may also be used, such as hexagonal, square, star-shaped, etc.

FIG. 2 shows a screw according to the invention having a body 20 supplied with a head 25 at one end thereof and a screw thread 22 along the outer surface of the body 20. Two cannulae 26 extend from the head 25 of the screw to its tip 28. The head 25 of the screw has an undersurface 24 that may be matched to a counter-sunk hole in bone or an implant.

FIG. 3 shows a soft tissue-to-bone anchor or suture anchor according to the invention. The anchor has a body 31 supplied with threads 32 on its outer surface, and has a top-end 33 supplied with means of securing a suture, in this instance, outwardly projecting flanges 31 through each of which extend holes 34 for receiving a suture. Cannulae 35 extend from the top end 33 of the anchor to the tip 36.

FIG. 4A is a schematic showing an interference screw 40 in an interference fit between a bone block or graft 42 and a portion of a bone structure in the body illustrated as vertebra 44. The bone graft 42, shown in perspective view also, has upper surface 42a and lower surface 42b that are respectively able to fuse with undersurface 41b (of vertebra 41) and uppersurface 44a (of vertebra 44). A further interference screw may be inserted, in interference fit, between graft 42 and vertebra segment 41. As shown, the threads of the interference screw 40 engage both the graft 42 and the bone structure 44 thereby holding the graft firmly in place. However, in an interference screw insertion procedure, there is no contact between graft and bone structure in the portion of the interface occupied by the screw so that fusion is delayed in this area until the screw is removed or absorbed, if an absorbable screw is used. Otherwise, fusion cannot take place.

Figure 4B:
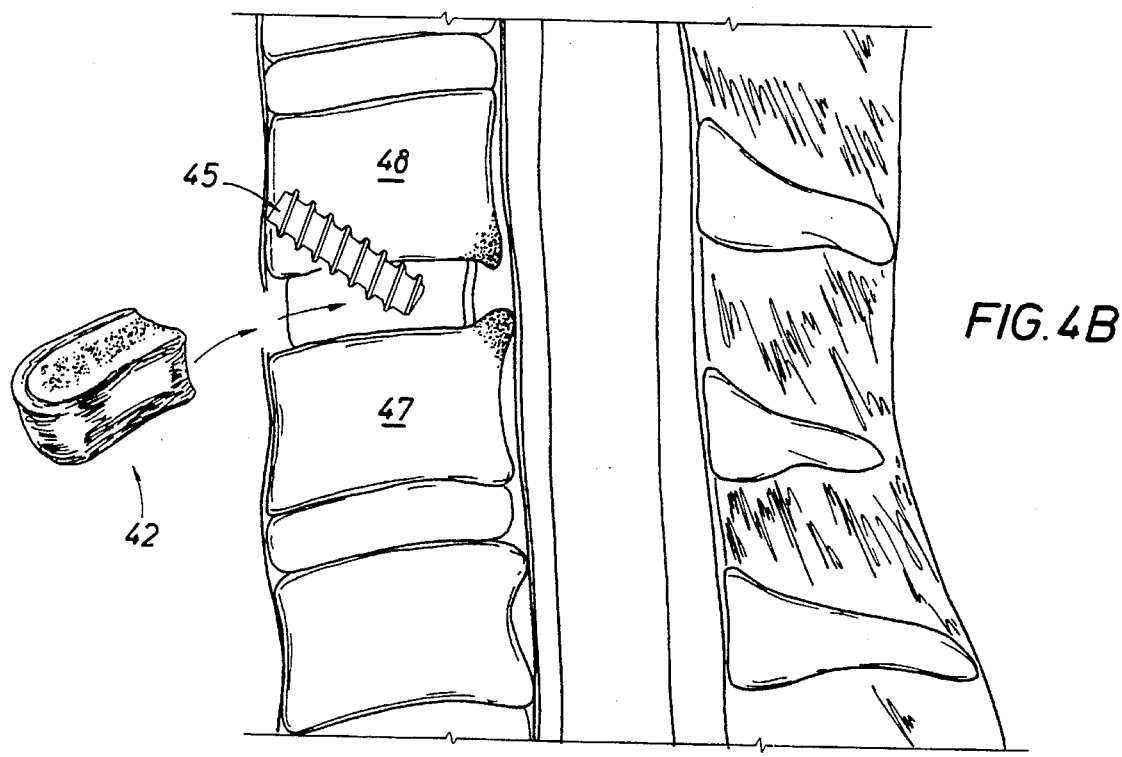
FIG. 4B is a schematic representation in partial cross-section of a screw according to the invention used as a "set screw" in replacing a disc with a bone graft in back surgery.

To overcome the obstacle to complete interfacial fusion posed by the interference screw procedure, the invention provides a "set screw procedure". FIG. 4B shows an interference screw according to the invention used as a "set screw." In this instance, a hole is first drilled at an angle through bone structure 48 into graft 47. The angle may vary depending upon access to the bone structure but should be such as to provide a secure set screw purchase in bone. Preferably, the angle is about 30° C. to about 60° C. to the bone graft—bone structure interface, most preferably about 45° C. Thereafter, interference screw 45 is torqued into place so that it engages both bone structure 48 and graft 47, as shown. Thus, the screw does not obstruct fusion and there is substantially full interfacial contact between graft and bone structure. This method is particularly advantageous when the screw is not bioabsorbable but is also effective when bioabsorbable screws are used.

The invention encompasses medical screws with multiple cannulae to reduce shear stress and thereby reduce the risk of shear failure of the screw during surgical implantation. As explained above, two cannulae are preferred.

In the case of invention screws fabricated from semicrystalline bioabsorbable polymers, it is preferred that the polymer be annealed to produce some degree of crystallization, to reduce residual stresses and improve dimensional stability. The degree of crystallization is one of the parameters that determine the rate of biodegradation and absorption of the material providing a mechanism for the gradual transfer of stress from the screw to the living tissue so that the tendency towards bone resorption is minimized.

Further, the bioabsorbable polymer composition may be impregnated with a variety of medicaments, depending upon specific requirements. These medicaments include antibiotics, anti-inflammatory agents, anti-clotting agents, and the like. In certain instances, it may be desirable to impregnate the screws with an osteoductive composition, such as bone morphogenic proteins, and osteoconductive compositions, such as hydroxyapatite, to encourage bony ingrowths into the screw. As the screw is bioabsorbed, the bony growth will facilitate fusion of a bone graft to the patient's bone structure, as required.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. A polymeric suture anchor of improved resistance to shear forces that arise during the torquing of the screw to affix a medical implant or graft to bone structure of a patient, the screw comprising:

an elongate body, comprising an organic polymer, the body having a longitudinal axis and an outer surface comprising means for engaging sides of a hole wherein the elongate body is adapted to fit;

one end of the elongate body comprising means for securing a suture; and at least two cannulae in the elongate body, said cannulae offset at a preselected distance from the longitudinal axis of the body, said cannulae sized for receiving means for applying torque to the body.

2. The anchor of claim 1, wherein the means for engaging comprises screw threads for turning the elongate body into the hole and engaging sides of the hole.

3. The anchor of claim 1, wherein the organic polymer of the elongate body comprises a bioabsorbable polymer selected from the group consisting of polylactic acid, polyglycolic acid, copolymers of lactic and glycolic acids, polycaprolactone, polydioxanone, polyalkylcarbonates, polyorthoesters and polyanhydrides.

4. The anchor of claim 1, wherein the body comprises a composite comprising a bioabsorbable polymeric matrix and a reinforcing material of bioabsorbable material.

5. The anchor of claim 4, wherein the bioabsorbable polymer is selected from the group consisting of polylactic acid, polyglycolic acid, copolymers of lactic and glycolic acids, polycaprolactone, polydioxanone, polyalkylcarbonates, polyorthoesters and polyanhydrides.

6. The anchor of claim 4, wherein the reinforcement is selected from the group consisting of absorbable organic polymer reinforcement, absorbable glass reinforcement, and absorbable ceramic reinforcement.

7. The anchor of claim 1, wherein the cannulae are of circular cross section.

8. The anchor of claim 7, wherein the circular cross section cannulae extend parallel to the longitudinal axis of the elongate body.

9. The anchor of claim 8, wherein the cannulae extend from one end of the elongate body to an opposite end.

10. The anchor of claim 1, wherein the organic polymer of the elongate body is selected from the bioabsorbable polymers and further comprises a medicament to promote healing.

* * * * *